(12) United States Patent
Lu et al.

(10) Patent No.: US 8,569,251 B2
(45) Date of Patent: Oct. 29, 2013

(54) USE OF MICROWAVE IRRADIATION FOR DELIVERY OF MACROMOLECULES

(75) Inventors: Qi Long Lu, Charlotte, NC (US); Pei Juan Lu, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 540 days.

(21) Appl. No.: 12/712,580

(22) Filed: Feb. 25, 2010

(65) Prior Publication Data
US 2010/0322911 A1    Dec. 23, 2010

Related U.S. Application Data

(60) Provisional application No. 61/155,331, filed on Feb. 25, 2009.

(51) Int. Cl.
*A61K 48/00*    (2006.01)

(52) U.S. Cl.
USPC ......... 514/44 R; 435/455; 435/468; 435/471; 424/93.21

(58) Field of Classification Search
None
See application file for complete search history.

(56) References Cited

U.S. PATENT DOCUMENTS

| 7,373,197 | B2 | 5/2008 | Daighighian et al. |
| 7,422,568 | B2 | 9/2008 | Yang et al. |
| 2004/0005294 | A1 | 1/2004 | Lee |
| 2006/0073597 | A1 | 4/2006 | Faris |
| 2006/0188437 | A1 | 8/2006 | Hong et al. |
| 2007/0135373 | A1 | 6/2007 | Li et al. |
| 2008/0208034 | A1 | 8/2008 | Yang et al. |

*Primary Examiner* — Jim Ketter
(74) *Attorney, Agent, or Firm* — Alston & Bird LLP

(57) ABSTRACT

The present invention is directed to methods of delivering macromolecules to a target cell or tissue by microwave irradiation. A target cell or tissue is exposed to one or more macromolecules to be delivered into the desired cell or tissue and irradiated with microwave radiation. The strength or power of the microwave radiation is such that the macromolecules are delivered into the target cell or tissue. Preferably, the strength of the microwave radiation does not significantly impact cell viability in a negative manner (e.g., apoptosis).

23 Claims, 9 Drawing Sheets

```
                        SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthesized

<400> SEQUENCE: 1
ggccaaacct cggcttacct                                              20

<210> SEQ ID NO 2
<211> LENGTH: 20
<212> TYPE: DNA
<213> ORGANISM: Artificial Sequence
<220> FEATURE:
<223> OTHER INFORMATION: Synthesized

<400> SEQUENCE: 2
aggtaagccg aggtttggcc                                              20

<210> SEQ ID NO 3
<211> LENGTH: 22
<212> TYPE: DNA
<213> ORGANISM: Artificial Sequence
<220> FEATURE:
<223> OTHER INFORMATION: Synthesized

<400> SEQUENCE: 3
cagaattctg ccaattgctg ag                                           22
```

-continued

```
<210> SEQ ID NO 4
<211> LENGTH: 20
<212> TYPE: DNA
<213> ORGANISM: Artificial Sequence
<220> FEATURE:
<223> OTHER INFORMATION: Synthesized

<400> SEQUENCE: 4
ttcttcagct tgtgtcatcc                                              20
```

USE OF MICROWAVE IRRADIATION FOR DELIVERY OF MACROMOLECULES

CROSS REFERENCE TO RELATED APPLICATION

This application claims the benefit of U.S. Provisional Application No. 61/155,331, filed Feb. 25, 2009, which is incorporated by reference herein in its entirety.

BACKGROUND OF THE INVENTION

1. Field of the Invention

The present invention relates generally to a method of delivering macromolecules, especially genes and oligonucleotides, into target cells or tissue by the use of microwave irradiation 2. Description of Related Art Gene and nucleic acid delivery systems can be divided into three major groups: (1) virus-mediated, (2) non-viral biochemical vectors; and (3) physical methods. Viral vectors, such as recombinant adenovirus, adeno-associated virus and herpes simplex virus, are very efficient in gene transfer both in vivo and in vitro. However, their safe applications in humans remain to be verified. Non-viral biochemical vectors, such as cationic liposomes, polymers and microbubbles, are relatively safe and easy to manufacture, but with limited efficacy, particularly in vivo. The main physical methods of transfection are electroporation and sonoporation. Electroporation has been shown to provide efficient gene delivery both in cultured cells and in tissues in vivo locally. However, tissue damage associated with high voltage may limit clinic applications. Sonoporation provides a safe alternative for controlled delivery of transgenes, but has so far achieved limited efficiency both in vitro and in vivo. Accordingly, difficulties with the non-destructive delivery of macromolecules into cells have limited the potential applications of antibodies, genes, enzymes, peptides, and antisense oligonucleotides in both laboratories and in the treatment of patients.

As such, there remains a need for a safe and efficient method of delivering one or more macromolecules to targeted cells or tissue. Further, a need remains for a method of delivering macromolecules into cells either in vitro or in vivo such that a patient can realize a therapeutic effect for a large variety of diseases and disorders.

BRIEF SUMMARY OF THE INVENTION

The present invention satisfies at least some of the aforementioned needs by providing a method of delivering macromolecules to a target cell or tissue by microwave irradiation. In one such embodiment, a target cell or tissue is exposed to one or more macromolecules to be delivered into the desired cell or tissue and irradiated with microwave radiation. The strength or power of the microwave radiation/energy is selected or controlled such the macromolecule is delivered into the target cell or tissue without significantly impacting cell viability in a negative manner (e.g., apoptosis). For instance, the microwave irradiation of cells or tissue should preferably not kill the targeted cells, but instead permeabilize the cells to allow the cells to effectively take-up the desired macromolecule (e.g., oligonucleotide or gene). As such, the step of irradiating the target cells or tissue with microwave radiation can form open pores in at least a portion of the cell or tissue. For example, irradiating target cells with microwave radiation can form several aqueous open pores in the cell membrane or tissue wall. Macromolecules can be introduced into the cells or tissue through these pores. Additionally, microwave radiation can also enhance the delivery of macromolecules through non-pore formation mechanisms.

Embodiments of the present invention provide methods to facilitate the delivery of macromolecules (e.g., genes and oligonucleotides) via microwave irradiation. In particular, certain embodiments of the present invention provide methods for the delivery of macromolecules into cells in vitro while other embodiments provide methods for the delivery of macromolecules into cells in vivo. For instance, one embodiment of according to the present invention utilizes the emittance/application of microwave radiation to deliver macromolecules into cells in culture for either an experimental or medicinal purpose. Alternatively, one embodiment utilizes the emittance/application of microwave radiation to deliver macromolecules into cells in living organisms for diagnostic and therapeutic purposes. In such embodiments, the delivery of macromolecules can beneficially include the delivery of therapeutic agents to treat a multitude of diseases and disorders (e.g., human diseases).

In preferred embodiments, the present invention provides a method for delivering macromolecules (e.g., genes and oligonucleotides) into targeted cells without killing or severely damaging the cell while allowing the treated cells to express a gene or utilize the oligonucleotide/oligmers to achieve a therapeutic effect. As such, embodiments of the present invention include the manipulation of the emittance of microwave radiation to provide a controlled and desirable energy level to achieve the desired biological effect on living cells. For instance, the microwave irradiation step can be controlled in several aspects including, but not limited to, adjusting (i) the power or strength of the microwave energy, (ii) the duration of emittance/application of the microwave energy, and (iii) frequency of emittance/application (e.g., number of cycles).

In one embodiment, macromolecules are delivered into a target cell provided within a cell culture. The cell culture comprises the target cell in a suitable culture medium. At least one macromolecule is added into the cell culture prior to or immediately after emittance of microwave radiation into the cell culture. The cell culture, including the macromolecule, is exposed to microwave radiation at a level in which at least one macromolecule is delivered into the target cell without destroying the target cell. In another embodiment, the present invention provides a method of delivering macromolecules to a target cell or tissue (e.g., liver or lung cells) on or within a living organism. Once the desired cells or tissue is identified, at least one macromolecule or a pharmaceutically acceptable formulation thereof can be administered onto or near the desired target cell or tissue by local or systemic delivery. The targeted cells or tissues are then exposed to microwave radiation. The macromolecules can be formulated as a solution, solid materials such as tablets, or any other forms suitable for use in living organisms. The formulations can contain any pharmaceutically acceptable adjuvants, such as for enhancing delivery, increasing the desired effect of the macromolecules, or targeting the specific cells or tissues. Preferably, the microwave radiation is provided at a level in which the macromolecule is delivered into the target cell or tissue without destroying or severely damaging the target cell or tissue. In other words, most of the cells or tissue exposed to irradiation should preferably not be killed or damaged. In such embodiments, the targeted cells or tissue can comprise an internal organ of a living organism.

In another aspect, the present invention provides a method of treating a living organism suffering from a genetic disease or disorder by delivering a macromolecule into a cell having a defective or faulty gene. The macromolecule is preferably administered onto or near a cell or tissue comprising the faulty gene by local or systemic delivery. The macromolecule for delivery into the cell having the faulty gene will be dictated by the particular disorder or disease associated with the faulty gene. In particular, the particular macromolecule for delivery should be capable of providing a therapeutic effect once delivered into the cell or tissue. The target cells having the faulty gene are irradiated with microwave radiation. In preferred embodiments, the microwave radiation is provided at a level in which the macromolecule is delivered into the cell or tissue without destroying the target cell or tissue. In certain embodiments, the cells comprise cells of internal organs. Accordingly, embodiments of the present invention provide a safe and effective method for providing in vivo gene/oligomer-mediated therapy.

In one alternative embodiment, the cell having the faulty gene can be removed from the living organism and placed in a viable culture medium. A macromolecule capable of providing a therapeutic effect once delivered into the cell or tissue is added to the cell culture. Preferably, after addition of the macromolecule the targeted cell is exposed to microwave energy. After irradiation of the cells, the treated cells are infused back into the living organism.

Thus, the present invention provides a safe and efficient method of delivering one or more macromolecules to targeted cells or tissue both in vitro and in vivo. Accordingly, the present invention also offers a safe method of providing gene therapy for a patient in need thereof. As such, a patient can realize therapeutic relief from a large variety of diseases and disorders.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

Figure 1:
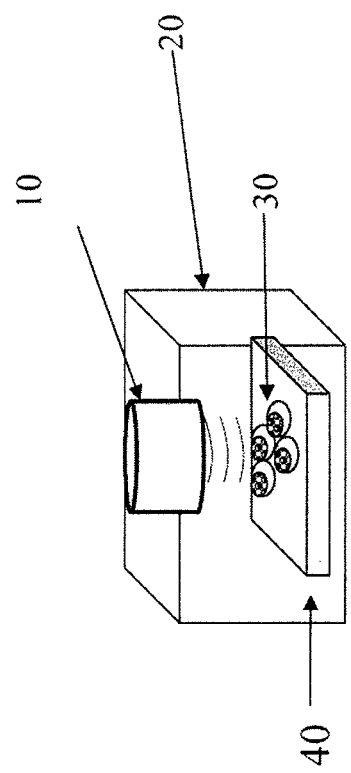
FIG. 1 illustrates the microwave irradiation of target cells for the delivery of a macromolecule according to one embodiment of the present invention.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements.

The present invention generally relates to methods of delivering macromolecules to a target cell or tissue by using microwave irradiation. For example, in accordance with embodiments of the present invention, macromolecules can be introduced into cells, such as eukaryotic cells, by exposing the targeted cells or tissue to at least one macromolecule and microwave energy/radiation. While not wishing to be bound by theory, it is believed that irradiating the target cells or tissue in the presence of one or more macromolecules causes the outer cell or tissue wall (e.g., cell membrane) to become permeable so that macromolecules are able to be introduced into irradiated cells or tissue. As discussed in greater detail below, irradiating cells/tissue with microwave radiation, according to embodiments of the present invention, can create or form aqueous open pores in the cell membrane through which a variety of macromolecules can be passed or inserted into the targeted cell or tissue. The irradiation of cells/tissue, according to certain embodiments of the present invention, can also affect the cell membrane by inducing an enhanced binding of the macromolecules to the cell membrane and movement of membrane molecules for more effective entry. In addition, the power and duration of the microwave radiation can be selected so that it does not significantly impact cell viability or function in a negative manner, such as causing cell death (e.g., necrosis or apoptosis), stopping cell proliferation or differentiation, or halting the performance of normal functions. As such, the present invention provides an effective method of introducing one or more macromolecules into a cell or tissue without causing a significant negative impact to the targeted cell or tissue. However, in certain alternative embodiments, the aim of the macromolecules is for cell destruction, that is to kill the cells such as for the treatment of cancers. In such embodiments, the power and duration of the microwave radiation can be adjusted to allow the targeted cells to die as well as to enhance the delivery of macromolecules.

In some embodiments, various chemical reagents, such as pluronic polymers, peptides, lipids and liposomes, or other delivery enhancers, gene expression enhancers, and dyes for tracing the micromolecules or the fate of the targeted cells can independently or simultaneously delivered into a target cell or tissue by microwave irradiation.

The present invention can be used to introduce a variety of different macromolecules into cells or tissue include a broad range of large molecular natural and synthetic biopolymers including, but not limited to, nucleic acids (including oligonucleotides), DNA, RNA, proteins, carbohydrates, lipids, dendrimers, plasmid DNA, genes (i.e., portion of an organism's DNA), and polysaccharides. Additionally, a macromolecule can include oligomers having different linkages between monomers or modified functional groups (including, but not limited to morpholino, peptide nucleic acids (PNA), 20-Methyl phosphorothioate, Locked Nucleic acids (LNA)), preferably in which they poses the ability to bind to complimentary DNA or RNA molecules. Such oligomers can preferably comprise of from 10 to 200 monomers, 50 to 150 monomers or 75 to 125 monomers (or alternatively the oligomers can consist of 20 monomers, 50 monomers, 75 monomers, or 150 monomers), and therefore are able to binding to targeted nucleic sequences of similar sizes, being 10 to 200 nucleic acids in length. Additionally, all of these different types of macromolecules can be delivered individually or in combination. Furthermore, such oligomers can be modified or linked together by any chemical groups as linkers as long as the oligomers are to be delivered with the use of microwave.

Microwaves are electromagnetic waves with the frequency ranging from 300 to $3 \times 10^5$ MHz. The energy released from the wave affects only the molecular rotation or movement and is not sufficient to cleave molecular bonds or affect molecular structure. The specific wavelength used for domestic cooking and heating devices is 2450 MHz. The same wavelength has also been used for scientific and medical applications, such as tissue ablation. The ability of the microwave irradiation to penetrate deep into biological materials with high efficiency for energy transfer has lead to the technique being widely used for food processing. Microwave irradiation can produce nearly instant temperature increase within its entire reaction volume and cause rapid movement of dipole molecules in solutions. Such properties have been proved to be of great value for improving efficiency and reducing the time of organic chemical synthesis. It is for these reasons that microwave irradiation has been extensively explored as an effective mediator and energy provider for organic chemistry.

The mechanisms by which microwave irradiation improves the delivery of macromolecules, such as plasmid DNA and oligonucleotides, are not fully understood. The energy from microwave irradiation consists of an electric field and a magnetic field, but only the electric field is considered to transfer energy to a substance within its reach. This energy transfer is conducted through two mechanisms, dipole rotation and ionic conduction. Dipole rotation is the reaction of the polar molecules to align themselves to the electric field of the microwaves. This interaction is related to the polarity of the molecules and their ability to align with the electric field. Similarly, ionic conduction is the result of alignment of free ions or ionic species to the microwave electric field. Although not desiring to be held to the following explanation, it is believed that the polar charges on the cell membrane molecules, such as proteins and lipids, may oscillate with the changing electric field of microwave irradiation, causing increased fluctuation of the cell membrane. These effects are possibly similar to those proposed to explain the mechanisms of two other physical methods for gene transfer, electroporation and ultrasound irradiation. Specifically, microwave irradiation may also induce dipole rotation and ionic conduction on the nucleic acids, which may lead to rapid movement of the molecules with increased opportunity to interact with and pass through the cell membrane, resulting in an increase in cellular uptake of nucleic acids. Our results, as shown in the "Examples" section of the present specification, indicate that the efficiency of microwave irradiation on nucleic acid delivery may depend on the size of the molecules, with short oligonucleotides being delivered much more efficiently than large plasmid DNA.

As such, the power and duration of microwave radiation applied to the targeted cells or tissue should be selected to create or form one or more aqueous open pores in the cell or tissue membrane (e.g., plasma membrane). The cell membrane (e.g., plasma membrane, plasmalemma, or "phospholipid bilayer") is a selectively permeable lipid bilayer found in all cells. The cell membrane contains a myriad of biological molecules, but mainly proteins and lipids. In one of its roles, the plasma membrane of a cell serves the vital function of partitioning the molecular contents of the cytoplasm from its external environment. However, the lipid matrix of the cell membrane can be disrupted by microwave irradiation, according to embodiments of the present invention, leading to an increase in transmembrane conductivity and diffusive permeability. These effects are the result of formation of aqueous pores in the membrane, movement of membrane components, or a combination thereof, which also alters the electrical potential across the membrane.

As referenced above, irradiating target cells or tissue is believed to permeabilize the outer cell membrane (e.g., plasma membrane) or tissue wall in the same or similar fashion as electroporation methods of transfection. That is, the irradiation of target cells or tissue may temporarily disrupt the outer cell membrane or tissue wall and forms open pores similar to conduits or passageways extending through the cell membrane to allow foreign material (e.g., macromolecules) to pass through these conduits and into the targeted cells or tissue. The formation of the open pores through the outer cell membrane is believed to be due at least in part to the oscillating electric field associated with microwave energy. The pores created by the microwave irradiation increase the permeability of the outer cell membrane or tissue wall such that the membrane now allows a greater passage of a variety of molecules. Prior to irradiation, for instance, a cell membrane may only permit a selected group of relatively small molecules or solutes, such as water or single nucleotide molecules, or individual amino acids to pass through by diffusion. When these cells are irradiated to create open pores extending through the outer cell membrane, a variety of macromolecules that could not previously diffuse into the cell are now allowed to be inserted into the cell by diffusion through the pores formed in the outer cell membrane.

According to embodiments of the present invention, macromolecules are allowed to diffuse into the targeted cells through the open pores formed in the outer cell membrane or tissue wall. The molecular diffusion of macromolecules can be understood as a net transport of the macromolecules from outside the targeted cell through the cell membrane and into the cell or tissue. The diffusion of the macromolecules into the targeted cells or tissue can be explained by the concentration gradient of the macromolecules across the cell membrane. Since the concentration of the macromolecules for delivery into the targeted cell is much greater than that inside the targeted cell, the macromolecules begin to randomly "move" to the lower concentration region inside the targeted cell. In certain embodiments, the microwave irradiation activates the movement of membrane or cell surface molecules and allow the macromolecules to gain access to the existing transmembrane transport systems (e.g., ion channels) and facilitate the entry of the macromolecules into cytoplasm and then to other destinations such as nuclei. In certain embodiments, the microwave irradiation-mediated delivery can be performed in the presence of pressure, such as by increasing blood volume or block the drain of the vein in the area of targeted delivery.

The irradiation of cells or tissue, according to embodiments of the present invention, provides a temporary increase in permeability of the cell membrane. More specifically, the cell membrane is disrupted upon and during exposure to microwave energy, but shortly after cessation of the irradiating the cells or tissue the outer cell membrane quickly returns to normal, causing minimal disruption of the cells' functions. That is, upon termination of irradiation the permeability of the cell membrane returns to normal with the introduced macromolecule retained inside the cells.

According to embodiments of the present invention, the sizes of the potential pores created by microwave irradiation can range from 10 to 500 nm in diameter, or 50 to 400 nm in diameter, 100 to 300 nm in diameter, or 150 to 250 nm in diameter. Alternatively, the pores created by microwave irradiation can range from 20 to 300 nm in diameter, 50 to 200 nm in diameter, or 50 to 100 nm in diameter. Accordingly, the pores can allow macromolecules such as a protein of several hundred of amino acids, or a transgene of up to 10 kb in size, or 1 kb to 10 kb, 3 kb to 8 kb in size, or 4 to 6 kb in size, into the cells.

A rapid rise in the temperature by microwave irradiation could also be responsible for increase in membrane permeability by enhancing the fluidity of the membrane molecules. However, Galvin et al. reported that an increase in membrane permeability does not depend on significant increase in system temperature. See Galvin M J, Hall C A, McRee D I. Microwave radiation effects on cardiac muscle cells in vitro. Radiat Res 1981; 86: 358-367. Similarly, attempts to measure the temperature at precise points of the culture wells during the microwave irradiation with the IR thermo imager (Raytek ThermoView Ti30) failed to reveal a definitive correlation between the temperature and the efficiency of transgene expression as shown in the "Examples" section of the present specification. In fact, the results suggest that increased temperature itself may not have a direct effect on transgene expression and therefore a specific amount of local heating is neither a necessary component nor indicative of effective gene delivery.

Generally, the power and duration (selected to create pores through the outer membrane of the targeted cell or outer wall of the targeted tissue) of microwave energy/radiation applied to the target cells or tissue is sufficiently strong enough to deliver the macromolecules into the target cell or tissue through the pores created in the outer membrane or wall of the targeted cells or tissue. Preferably, the power level of the microwave radiation is selected so that it does not severely damage or kill a large percentage of the target cells. Most preferably, the microwave energy is controlled or selected such that the target cells or tissue are exposed to a level of radiation which does not severely damage a majority or any of the targeted cells. For instance, the power setting of the microwave radiation emitting device used to emit or expose the target cells to radiation can be controlled by manipulating the power setting, frequency of exposure, and time duration of exposure such that less than 30%, 20%, or 10% of the targeted cells are severely damaged or destroyed. In particular, it may be desirable to select a power and duration of exposure so that less than about 1 to 5% of the targeted cells or tissue are severely damaged or killed. Most preferably, none of the targeted cells or tissue are severely damaged (e.g., the cells survive but lose part or most of their normal functions) or killed.

As such, embodiments of the present invention can include controlling the level of microwave radiation applied to the target cell or tissue such that the irradiation step does not kill or severely damage the cells but permeabilizes the cells and allows take up of macromolecules (or smaller molecules if desired).

In alternative embodiments, the power and duration (selected to create pores through the outer membrane of the targeted cell or outer wall of the targeted tissue) of microwave energy/radiation applied to the target cells or tissue can also be adjusted to allow for the killing of some of the targeted cells or tissues when the aim or desired function or purpose of the delivered macromolecules is to destroy the targeted cells or tissues. This is commonly encountered for the treatment of cancers with the gene/oligomer therapy according to certain embodiments of the present invention. For instance, the power setting of the microwave radiation emitting device used to emit or expose the target cells to radiation can be controlled by manipulating the power setting, frequency of exposure, and time duration of exposure such that up to 10%, 20%, or 30% of the targeted cells are severely damaged or destroyed. In particular, it may be desirable to select a power and duration of exposure so that a maximal degree of cell death is achieved by irradiation as well as delivery of the macromolecules in the rest of the targeted cell population.

In several embodiments, the process of irradiating target cells or tissue with microwave energy is carried out with the use of a magnetron capable of emitting electromagnetic waves with a frequency ranging from 300 to $3 \times 10^5$ MHz. A magnetron is a tube that generates non-coherent microwaves and utilizes electrical and magnetic currents in order to create an intense power of microwave energy, which is typically used in microwave ovens. The electromagnetic energy created from a magnetron is the same type of energy used in radio and television broadcasting. A magnetron tube has a filament in the center which heats up when it is exposed to a slight amount of voltage or energy. The filament gives off electrons as it becomes hotter. These electrons move outward in search of positive anodes, or electrodes, but they come in contact with a negative magnetic field along the way. The negative magnetic field within the magnetron repels the electrons. As a result, they become stuck in one area and begin rotating in circles. This creates more heat, as well as a supply of energy strong and hot enough to quickly heat an item.

According to embodiments of the present invention, the power output or selected power setting of the microwave radiation emitting device (e.g., magnetron) can range from about 50 Watts to about 5000 Watts, or about 50 Watts to about 4000 Watts, or about 100 Watts to about 3000 Watts, or about 100 Watts to about 2000 Watts, or 200 Watts to about 1000 Watts. In certain embodiments, the power output or selected power setting of the microwave radiation emitting device (e.g., magnetron) can range from about 200 Watts to about 300 Watts, while in certain preferred embodiments the power output or setting can range from about 400 Watts to about 500 Watts.

In addition to manipulating the power or output of the microwave radiation for irradiating targeted cells or tissue by controlling and/or selecting the appropriate microwave energy emitting device, the irradiation of targeted cells or tissue can also include controlling the frequency and time duration of exposure to microwave radiation. For example, the targeted cells or tissue can be exposed to an appropriate level of microwave energy in a single application of microwave radiation. In other embodiments, the targeted cells or tissue are exposed to an appropriate level of microwave energy in a series of one or more cycles. In such embodiments, each cycle comprises a time duration in which the targeted cells or tissue are exposed to microwave radiation followed by a second time duration in which the targeted cells or tissue are not exposed to microwave radiation. In certain embodiments, the time duration in which the targeted cells or tissue are exposed to the microwave radiation is the same as the time duration in which the targeted cells or tissue is not exposed to the microwave radiation. As merely one example, a group of target cells can be treated by irradiating the cells with microwave energy in a series of 5 cycles where each cycle includes 5 seconds of exposure followed by 5 seconds of no exposure. In various embodiments, however, the number of cycles and the respective time durations can be altered. For instance, the number of cycles can range from 1-100, 2-100, 2-50, 2-30, 2-20, or 5-15. Likewise the time duration of exposure can be independently varied. For example only, the time duration of exposure can range from 1 millisecond to 5 minutes, 1 millisecond to 3 minutes, or 1 millisecond to 1 minute, or 1 millisecond to 1 second. In other embodiments, the time duration of exposure can range from less than 1 second (e.g., 1-5 tenths of a second) to 1 minute, 1 second (or 1-5 tenths of a second) to 45 seconds, 1 second (or 1-5 tenths of a second) to 30 seconds, 1 second (or 1-5 tenths of a second) to 20 seconds, 5 seconds to 20 seconds, or 3 seconds to 15 seconds. Furthermore, embodiments of the present invention can include exposure cycles that are different and independent of each other. By way of a non-limiting example only, one method can treat targeted cells with the use of two cycles. The first cycle can comprise irradiating the targeted cells for 5 seconds followed by 5 seconds of non-exposure and the second cycle can comprise irradiating the cells for one-tenth of a second followed by a period of non-exposure.

In certain preferred embodiments, the time duration in which the targeted cells or tissue are exposed to the microwave energy can be different than the time duration in which the targeted cells or tissue are not exposed to the microwave radiation. Preferably, the time duration in which the targeted cells or tissue are not exposed to the microwave energy is longer than the time duration in which the targeted cells or tissue are exposed to the microwave radiation. Further, the time durations of each cycle can be selected independently of each other. For instance, embodiments of the invention can include a step of irradiating target cells or tissue in a series of 2 to 100 cycles where the time duration of exposure of one or more cycles is different from the others. For example, the methods according to embodiments of the present invention can include irradiating cells over the course of three cycles. The first cycle can include an exposure duration of 12 seconds followed by 30 seconds of non-exposure. The second cycle can include an exposure duration of 6 seconds followed by 45 seconds of non-exposure. The third cycle can include an exposure duration of 3 seconds followed by a period of non-exposure. As discussed above, the number of exposure cycles can be varied depending on the particular needs and sensitivity of the cells at hand. For instance, the treatment of cells or tissue can include a series of exposures to microwave radiation ranging from 2 to 100 cycles. 2-100; 2-50; 2-30; 2-20; 2-10; 5-20; 5-15; or 5-10 cycles.

In certain embodiments, the macromolecule delivered into target cells or tissue comprises oligonucleotides suitable for interference of gene expression (such as oligonucleotides or their analogues to destroy targeted mRNA), protein function (such as oligonucleotides or their analogues to binding targeted protein), splicing regulation (such as oligonucleotides or their analogues to include or exclude one or more specific exons) or modification of genomic sequence (such as oligonucleotides or their analogues to correct disease-causing point mutations).

In certain preferred embodiments, the macromolecule is formulated with an additional reagent or reagents suitable for enhancing the delivery of the macromolecule. For instance, the macromolecules can be formulated as solution, solid materials such as tablets, or any other forms suitable to be used in living organisms. The formulations can contain any adjuvants such as lipids, liposomes or other polymers (such as pluronics) for the purpose of enhancing delivery, effect of the macromolecules or targeting the specific cells or tissues.

According to particular embodiments of the present invention, a method of delivering macromolecules to target cells in vitro is provided. In one embodiment, a cell culture including target cells in a suitable medium is provided. A macromolecule to be delivered into the target cells is added to the cell culture, thereby exposing the target cells to the macromolecule. The cell culture is then irradiated by exposing the cell culture to microwave radiation. Preferably, the level of microwave radiation is selected such that the macromolecule is delivered into the target cells without destroying or severely damaging most of the target cells.

FIG. 1 illustrates one application of microwaved-mediated delivery of macromolecules according to one embodiment of the present invention. A microwave generator (e.g., magnetron) 10 is located within a microwave chamber 20 in which the microwaved-mediated delivery of macromolecules is performed. Cells or tissue samples 30 are generally placed or grown in, but not limited to, plastic culture carriers 40. Once the samples 30 are positioned within the microwave chamber 20 and a desired macromolecules has been added to the cell culture, the microwave generator 10 is turned on to begin irradiating the cells or tissue.

Figure 2:
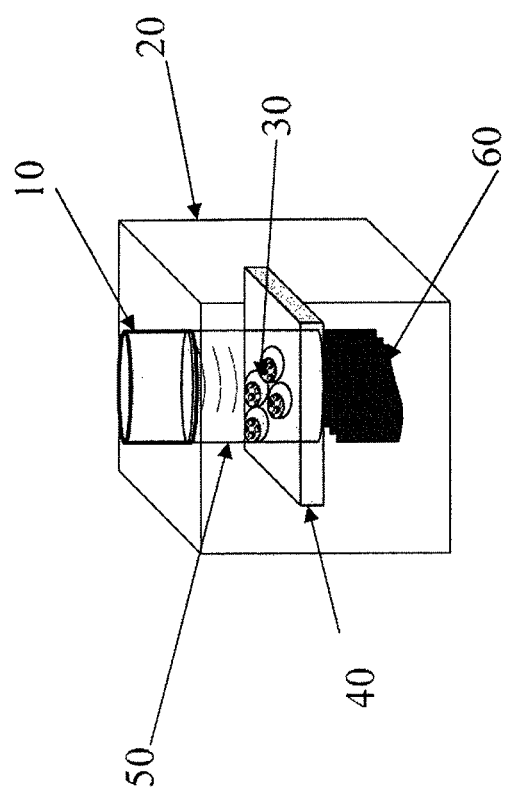
FIG. 2 illustrates the microwave irradiation of target cells utilizing a path chamber and an microwave radiation absorber according to one embodiment of the present invention.

FIG. 2 illustrates another embodiment of the present invention. In this particular embodiment, the distribution of microwave energy is more controlled by utilizing a microwave path chamber 50 and a radiation absorbent material 60 positioned under the culture carrier 40. The microwave chamber path 50 conducts the microwave energy to the targeted site. As such, the microwave chamber path 50 can be configured to have any desirable size and depth. Preferably, the microwave path chamber 50 is sealed so that minimal to no microwave energy is leaked outside of the path chamber. Suitable chamber paths are commercially available and used in various tissue ablation devices. If needed, such chamber paths can be structurally modified for specific applications. Additionally, a radiation absorbent material 60 is positioned under the culture carrier 40 so that any microwave energy passing through the samples is absorbed and prevents further exposure of the cells to random and uncontrollable microwave energy. Thus, the targeted cells or tissue can be exposed to a directional and evenly distributed level of microwave energy. In preferred embodiments, the culture carrier is made from material which absorbs, but does not reflect or bounce microwave energy around within the chamber. These embodiments provide a controlled and even distributed microwave energy for the irradiation of target cells or tissue and delivery of macromolecules in vitro and in vivo in model organisms.

In one alternative embodiment, the radiation absorbent material 60 can be integrated into part (or the entirety) of the structure of the carrier 40. Additionally, the radiation absorbent material can also be non-reflective to microwave energy. In one embodiment, the radiation absorbent material can be replaced with a non-absorbent material that is non-reflective to microwave energy. The absorbent material, non-absorbent but non-reflective material, or combination thereof can be integrated into the structure of carrier for the targeted cells or tissues. The microwave chamber can also be constructed with any or both of these types of materials.

In certain embodiments, macromolecules are delivered to cells or tissue in vivo. In such embodiments, the cells or tissue can include a local area on or within a living organism. In particular embodiments, the targeted cells or tissue can be a portion of an organ (e.g., internal organs such as the liver, lungs, or heart) or an entire organ. In preferred embodiments, the targeted cells or tissue is a portion of an internal organ or an entire internal organ. In one alternative embodiment, an entire living organism or being can be irradiated to effectively provide a systemic delivery to one or more macromolecules.

In one embodiment, the method of delivering macromolecules to target cells or tissue on or within a living organism includes the administration of one or more macromolecules onto or near the target cell or tissue through local (e.g., injection with any suitable device or other applications such as dropping onto the target cell) and/or systemic (e.g., by blood circulation) administration followed by exposing the target cells or tissue to microwave radiation. As such, the administration of the macromolecules, according to certain embodiments, can by orally or intravenous (e.g., vein or artery injection). Preferably, the microwave radiation is provided in a controlled manner and at a level in which the macromolecules are delivered into the target cells or tissue without destroying or severely damaging a substantial portion of the targeted cells or tissue, unless such targeted cells or tissues are targeted for destruction.

Figure 3:
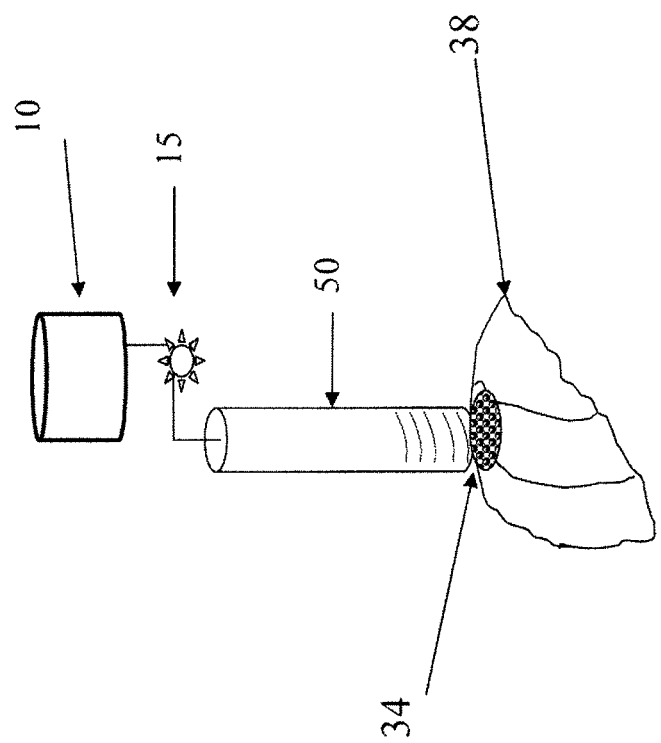
FIG. 3 illustrates the microwave irradiation of a tissue area of a body part for the delivery of a macromolecule according to one embodiment of the present invention.

As shown in FIG. 3, targeted cells or tissue 34 on a viable body part 38 of a living organism can be irradiated with microwave radiation in a controlled manner and at an acceptable level for the delivery of macromolecules without destruction of the targeted cells or tissue. In the particular embodiment exemplified by FIG. 3, a microwave generator 10 such as a magnetron is utilized as the source of microwave energy to mediate the delivery of the macromolecules. The microwave energy output can be controlled by the power output control 20. In such embodiments, the power output control 20 is manipulated to select the desired power output. The microwave energy is conducted through microwave path chamber 50 to provide a focused and evenly distributed application of microwave energy to the targeted cells or tissue 34. As illustrated by FIG. 3, the microwave path chamber can be selected to have any desirable size or shape to better isolate specific areas of organs for treatment without impacting the surrounding tissue. As such, the microwave chamber path should be positioned such that the targeted cells or tissue is aligned with the outlet of the microwave chamber path to receive maximal exposure whereas the untargeted cells or tissues are minimally exposed.

In various embodiments, an internal organ can be treated by aligning the target cells or tissue with a microwave radiation source via the microwave irradiation path chamber which operatively connects the radiation source to the targeted cells or tissue. In certain embodiments, the alignment of the target cells or tissue with the microwave radiation source comprises inserting the microwave path chamber through a canula which has been inserted into the living organism. The inserted canula provides a passageway for the microwave path chamber. As such the microwave path chamber is feed though the canula such that the end or outlet of the microwave path chamber terminates proximate to and substantially aligned with the target cells or tissue. Preferably, the path chamber is designed such that minimal to no microwave energy leaks out of the chamber.

In various alternative embodiments, the delivery of macromolecules into cells or tissue is carried out by the combination of microwave irradiation and a secondary delivery method selected from virus-mediated, non-viral biochemical vectors, electroporation, and sonoporation. In such embodiments, the second delivery method further enhances the delivery efficiency of the macromolecules. In certain embodiments, the secondary delivery method comprises utilization of lipopolymers, cationic polymers, ultrasound or microbubbles.

In certain embodiments, the secondary delivery method can include any known method for transfecting cells. In general, the delivery of molecules into a cell is defined as transfection. As such transfection includes the introduction or delivery of foreign material into eukaryotic cells using a virus vector or other means of transfer. Various known methods for transfection suitable as a secondary delivery method are described below. Transfection of animal cells typically involves opening transientpores or 'holes' in the cell plasma membrane, to allow the uptake of material. Genetic material (such as plasmid DNA or siRNA constructs), or even proteins such as antibodies, may be transfected into cells. In addition to electroporation, transfection can be carried out by mixing a cationic lipid with the material to produce liposomes, which fuse with the cell plasma membrane and deposit their cargo inside.

Other methods use highly branched compounds (e.g. dendrimers) to bind the genetic material (e.g. DNA, RNA, or miRNA) and get it into the cell. Another method is the inclusion of the genetic material to be transfected in liposomes, i.e. small, membrane-bounded bodies that are in some ways similar to the structure of a cell and can actually fuse with the cell membrane, releasing the genetic material into the cell. For eukaryotic cells, lipid-cation based transfection is more typically used.

Another method is the use of cationic polymers such as DEAE-dextran or polyethylenimine. The negatively charged genetic material binds to the polycation and the complex is taken up by the cell probably via endocytosis.

A direct approach to transfection is the gene gun, where the genetic material is coupled to a nanoparticle of an inert solid (commonly gold) which is then "shot" directly into the target cell. The genetic material can also be introduced into cells using viruses as a carrier. In such cases, the technique is called viral transduction, and, the cells are said to be transduced. Other methods of transfection include nucleofection, electroporation, heat shock, magnetofection and proprietary transfection reagents such as Lipofectamine, Dojindo Hilymax, Fugene, jetPEI, Effectene or DreamFect.

U.S. Pat. No. 5,942,634, incorporated herein by reference, describes the use of cationic amphiphiles to facilitate transport of biologically active (therapeutic) molecules into cells. U.S. Pat. No. 5,942,634 also teaches how to make therapeutic compositions incorporating a therapeutic molecule by contacting a dispersion of one or more cationic amphiphiles with the therapeutic molecules. The therapeutic molecules that can be delivered into cells include DNA, RNA, and polypeptides. Such compositions can be used to provide gene therapy, and delivery of antisense polynucleotides or biologically active polypeptides to cells.

In yet further embodiments, the present invention provides a method of treating a living organism suffering from a genetic disease or disorder by inserting/delivering a macromolecule (e.g., a gene) suitable for combating the particular genetic disease or disorder. In general, gene therapy is the insertion of genes into an organism's cells and tissues to treat a disease or disorder, and hereditary diseases in which a defective mutant allele is replaced with a functional one. Currently, there are a variety of different approaches to replacing or repairing the genes targeted in gene therapy. For example, a normal gene may be inserted into a nonspecific location within the genome to replace a nonfunctional gene. Alternatively, an abnormal gene can be swapped for a normal gene through homologous recombination. An abnormal gene can also be repaired through selective reverse mutation, which returns the gene to its normal function. Further, the regulation (the degree to which a gene is turned on or off) of a particular gene can be altered. Typically, however, gene therapy is carried out by inserting or delivering a "correct copy" or "wild type" gene into the genome. Customarily, the inserted gene is not necessarily an exact replacement of the "abnormal" or "faulty" disease-causing gene. Instead the replacement gene delivered into the cells is typically extra, correct copies of genes provided to complement the loss of function. A carrier called a vector must be used to deliver the therapeutic gene to the patient's target cells. Currently, the most common type of vectors are viruses that have been genetically altered to carry a piece of normal human DNA (in general called a gene). Viruses encapsulate and deliver their genes to human cells. Scientists have tried to harness this ability by manipulating the viral genome to remove disease-causing genes and insert therapeutic ones. Target cells such as a patient's liver or lung cells are infected with the vector virus, which unloads its genetic material containing the therapeutic human gene into the target cell. The generation of a functional protein product from the therapeutic gene restores the target cell to a normal cell. However, embodiments of the present invention negate the need for use of a carrier such as a vector. Unlike traditional methods, embodiments of the present invention provide gene therapy by delivering the replacement macromolecule into the targeted cells or tissue by microwave radiation which has not been considered possible until the present invention.

In one embodiment of the present invention, the method of treating a living organism suffering from a genetic disease or disorder includes the administration of one or more macromolecules onto or near a cell or tissue having a faulty gene. The macromolecule should be suitable for providing a direct or indirect therapeutic effect once delivered into the cell or tissue. Once the targeted cells or tissue have been exposed to the macromolecule, the cells or tissue are exposed to microwave radiation as described throughout the present specification. In one alternative embodiment, the targeted cells are removed from the living organism and placed in a viable medium prior to adding the macromolecule to the medium and irradiating with microwave energy. After irradiation, the treated cells are infused back into the living organism. In one such embodiment, the targeted cells comprise blood cells (e.g., white blood cells).

The macromolecule inserted into the targeted cells or tissue is generally not limited according to embodiments of the present invention. For instance if a particular macromolecule is currently recognized as either treating or potentially treating any disease or disorder, such a macromolecule can be inserted into the desired cells or tissue according to embodiments of the present invention. Further, the future discovery, identification or development of any particular macromolecule capable of providing a direct or indirect therapeutic effect to combat a disease or disorder is contemplated by embodiments of the present invention. For example, the macromolecule for delivery into targeted cells for purpose of providing therapy can include any of the following: a natural or synthetic oligonucleotide/oligomer adapted to inactivate the genes involved in the disease or disorder; an antisense oligonucleotide/oligomer specific to the faulty gene; RNA configured to signal the cell to cleave specific unique sequences in the mRNA transcript of the faulty gene, whereby translation of the faulty mRNA is disrupted and therefore expression of the faulty gene; double stranded oligodeoxynucleotide decoys capable of binding transcription factors that are required to modulate the transcription of the faulty gene, whereby the transcription factors bind to the decoys instead of the promoter of the faulty gene; single or double stranded DNA oligonucleotides capable of promoting a single base change within the faulty gene, wherein the oligonucleotide is designed to anneal with complementarity to the faulty gene with the exception of a target base which serves as the template base for repair.

EXAMPLES

In the study described below, the ability of the electromagnetic field and the thermal effect conferred by microwave irradiation to increase the fluidity of cell membranes and the enhancement of the movement of macromolecules, thus improving the entry of therapeutic agents into the cells, was examined. A laboratory-grade microwave-irradiating device (e.g., a magnetron) was used with variation in power and duration for the delivery of both oligonucleotide/oligomer and plasmid DNA into cultured myo-blasts.

I. Delivery of Macromolecules Into Cells

A. Gene Delivery with Luciferase (i.e., a Reporter)

Figure 4:
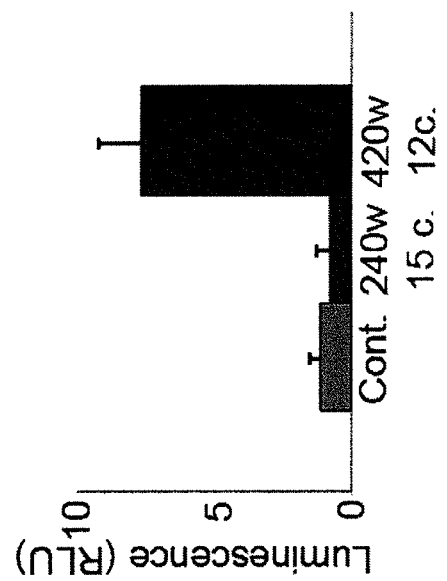
FIG. 4 shows a comparison of luciferase expression between a cell control group and those exposed to microwave radiation.
Figure 5:
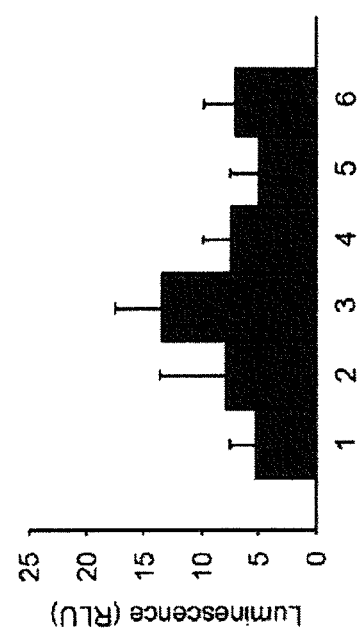
FIG. 5 shows the average luciferase expression at multiple well positions of a six-well plate.

The effect of microwave irradiation on the delivery of macromolecules into cells was first examined for gene delivery using a luciferase expression plasmid that allows the levels of reporter expression to be quantified. From preliminary data, two power settings with variation in duration and the number of cycles were investigated. At power settings of 240 and 420 W, a variety of exposure durations were attempted. The increase in luciferase expression was limited when the cells were exposed to 240 W for 5 s with six cycles. As shown in FIG. 4, luciferase activity improved when 15 cycles of irradiation were applied, but still not significantly different from the control cells without exposure to microwave irradiation. This is mainly due to the considerable variation between different wells of the same six-well plat as shown in FIG. 5. FIG. 5 shows the average luciferase expression at each well position of the six-well plate. Although some wells showed similar enzyme activity as the control, some wells clearly showed higher levels of the luciferase reading. For example, FIG. 5 shows that well number 3 exhibited an average Reflective Light Unit (RLU) of just under 15. These variable results within the same six-well plate are consistent with the highly uneven distribution of microwave energy within the irradiation chamber. When 420 W was used at 5 s per cycle, significantly higher levels of luciferase expression were observed after 6-15 cycles. The maximum efficiency of luciferase expression was achieved in the cells after 12 cycles of exposure with the average luciferase reading eight times higher than that in control cells and the cells with 240 W exposures (as seen in FIG. 4). However, variation between different wells of the same six-well plates remained since the same microwave irradiating device was used. Power settings higher than 420 W induced a rapid temperature increase, resulting in the death of most cells. However, the higher power levels may still be of value for gene delivery when the time duration of exposure is reduced (e.g., less than 1 second) and a more even distribution of microwave irradiation is achieved, for example, by one of the designs illustrated herein.

B. Variability of Delivery

The luciferase reporter assays indicated a variable nature in the distribution of the microwave irradiation within the chamber of the device currently available. To further investigate whether such variations for gene delivery exist within the same well of the culture plate, an enhanced green fluorescent protein (eGFP) expression vector was used because its expression can be directly visualized under fluorescence microscope and the distribution of the eGFP-expressing cells can be evaluated within a particular well. A setting of 420 W output with 12 cycles was utilized for irradiating the cells.

Figure 6:
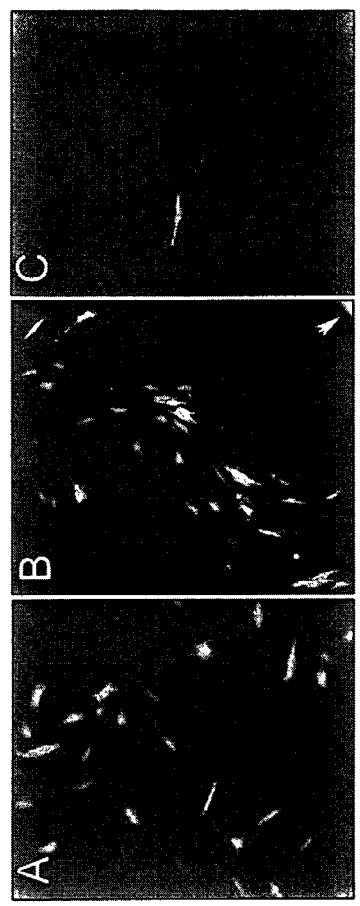
FIG. 6 shows a comparison of eGFP expression in C2C12 cells between a control group and those exposed to microwave irradiation.

After 24 h, eGFP expression was observed clearly only in some wells of the plates, as shown in FIG. 6. FIG. 6 shows a comparison of eGFP expression in C2C12 cells between a control group (i.e., Image C of FIG. 6) and those exposed to microwave irradiation (i.e, Image A of FIG. 6). Furthermore, the eGFP-positive cells were limited to some areas within a single well. As illustrated by image B of FIG. 6, strong eGFP expression was most frequently seen as a narrow ring at about two-third of the distance from the center of the well, although eGFP-positive cells were also present sporadically throughout the whole well.

C. Cell Viability

Figures 7A, 7B, 7C:
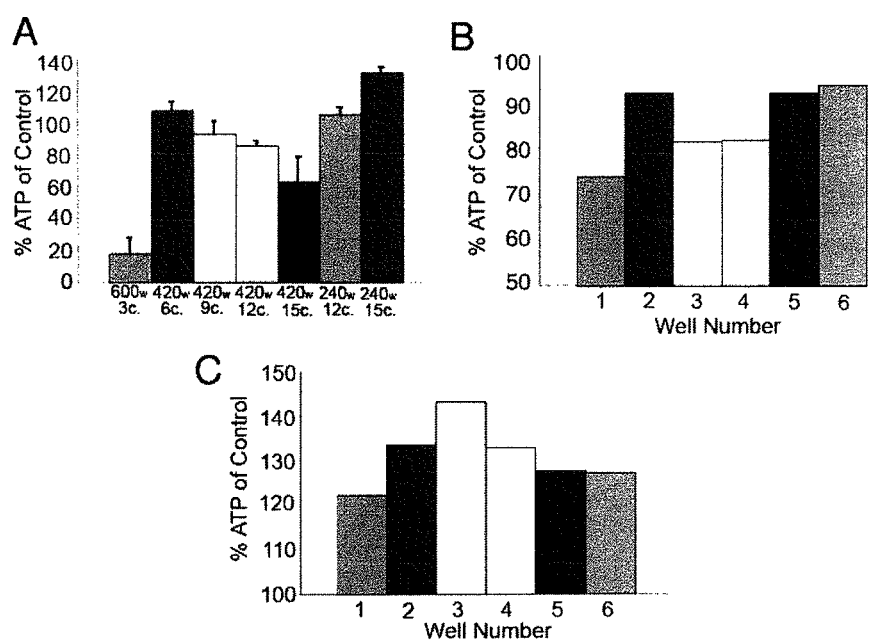
FIG. 7A illustrates the average cell viability after microwave irradiation across experimental groups.
FIG. 7B illustrates the cell viability of individual wells after microwave irradiation at 420 Watts for 12 cycles.
FIG. 7C illustrates the cell viability of individual wells after microwave irradiation at 240 Watts for 15 cycles.

All physical methods for gene delivery so far rely on its ability to temporarily permeabilize the cell membrane for nucleic acid entry without causing substantial cell damage or death. As such, the effect of the microwave irradiation with the settings for the delivery of plasmid DNA or other forms of transgene (such as synthetic or PCR products) on cell viability with ATP activity as an indicator was examined. 24 h after irradiating with microwave radiation, ATP activity was measured and compared with untreated control cells (as 100%). As shown in FIG. 7A, when the power was set at 600 W the average metabolic activity of the cells was reduced to only 18% of the control levels. FIG. 7A illustrates the average cell viability after microwave irradiation presented as relative percentages to the activity of ATP in untreated cells, where the percentage value it obtained from 6 wells across experimental groups. Considerable variation was observed in individual wells of the same culture plates with ATP activity ranging from less than 5% to 50% of the control levels.

As also illustrated in FIG. 7A, ATP activity was on average 90-60% of the control levels when the cells were exposed to 420 W for 9-15 cycles with 5 s for each cycle. At six cycles, ATP levels were at 100-105% of control. FIG. 7B illustrates the cell viability of individual wells irradiated at a setting of 420 W for 12 cycles. As shown in FIG. 7B, a setting of 420 W for 12 cycles of exposure, which produced the highest transgene expression, reduced the ATP activity to an average of 85% of the control levels. The results suggest that delivery of trans-genes into the cells by microwave irradiation is associated with limited levels of cell damage temporarily.

FIG. 7C illustrates the cell viability of individual wells irradiated at a setting of 240 W for 15 cycles. As shown in FIG. 7C, the percent ATP relative to the ATP activity in untreated cells was greater than those reported for irradiation at the higher power settings. Interestingly the metabolic activity increased consistently when the cells were exposed to 240 W for both 12 and 15 cycles as well as with 420 W for 6 cycles (FIG. 7A). A maximum increase up to 35% (average for six wells) was observed in the wells exposed to 15 cycles of 240 W (FIG. 7C). These results demonstrate the dual effect of microwave irradiation: it damages cells at high output, but it is able to enhance metabolism of target cells when applied at appropriate levels. This also raises the possibility that delivery of transgenes by microwave irradiation can be achieved with minimal cell damage.

To determine if there was any correlation between the temperature and the eGFP or luciferase expression, temperatures within each well were captured by infrared (IR) image. The treatment with 420 W 5 s for 12 cycles was used as it promoted higher levels of transgene expression than any other irradiation settings. Similar to eGFP expression, temperature readings at the various regions within and between wells of culture plates were highly variable. However, no correlation was evident when heat signatures from the samples were compared with the patterns of eGFP expression under the same treatment. It is therefore considered that the delivery of transgenes by microwave irradiation is not simply a thermal effect previously considered on biological materials.

D. Oligonucleotide Delivery

Figure 8:
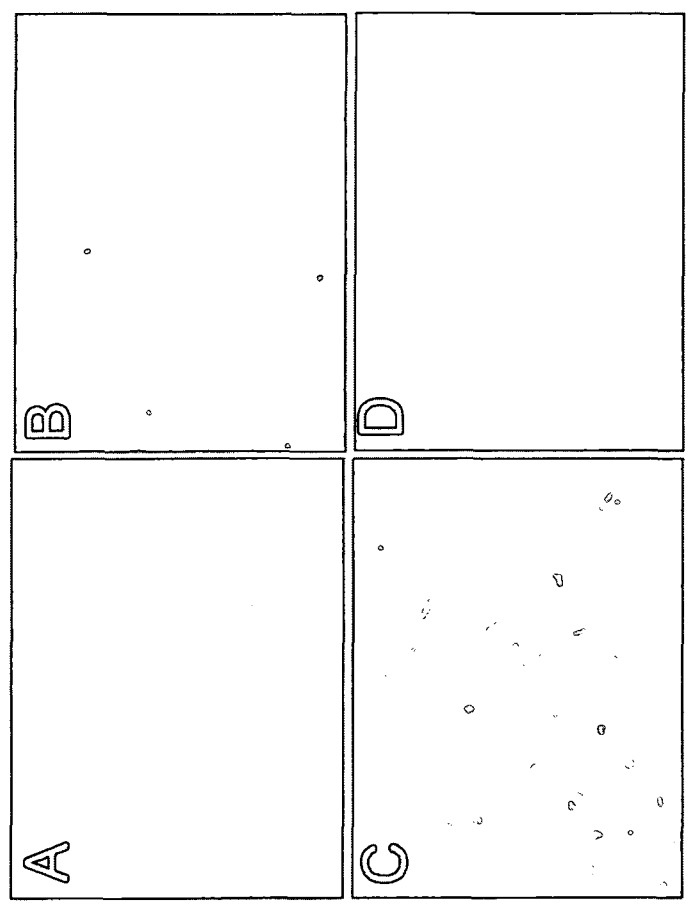
FIG. 8 shows a comparison of 2-O-methyl-phosphorothioate oligonucleotide delivery in C2C12 cells exposed to microwave irradiation and cells not irradiated with microwave radiation.

A previously established 20 mer antisense oligonucleotide (AON) (referred as E23+2-18) was used to target the junction sequence of exon 23 (2 bases from 30 of the exon 23) and intron 23 (18 bases from 50 of the intron 23) of the mouse dystrophin pre-mRNA. This oligonucleotide is able to specifically remove the dystrophin exon 23. E23+2-18 was initially synthesized as 2'O methyl-phosphorothioate oligonucleotides (2OMePS, negatively charged) and labeled with CY3 for direct visualization. The output of the microwave energy was set at 240 and 420 W for 5-s exposure with varying number of cycles and interval time of 5 and 45 s, respectively. The cells were then viewed under fluorescence microscope 10 min after microwave irradiation. Cells exposed to the CY3-tagged 2OMePS AON without microwave irradiation treatment showed barely detectable signals for CY3 (FIG. 8). In particular, FIG. 8 includes 4 images to provide a comparison of 2-O-methyl-phosphorothioate oligonucleotide delivery in C2C12 cells irradiated with microwave energy and cells not irradiated with microwave energy. Image A of FIG. 8 illustrates the results of cells exposed to the CY3 tagged oligonucleotides and irradiated at a setting of 420 W for 9 cycles, while Image B illustrates the results of cells exposed to the CY3 tagged oligonucleotides and irradiated at a setting of 420 W for 12 cycles. Image C of FIG. 8 illustrates the results of cells exposed to fluorescein-tagged oligonucleotides and irradiated at a setting of 420 W for 12 cycles. Image D of FIG. 8 illustrates the results of cells exposed to fluorescein-tagged oligonucleotides, but not exposed to microwave radiation. No significant increase in intracellular CY3 signal was observed when 240 W was used for 6-12 cycles. However, the levels of intracellular CY3 signal increased significantly when the power of microwave irradiation output was raised to 420 W with the increase in exposure cycles. Nearly all cells were transfected as demonstrated by high levels of CY3 fluorescence within cytoplasm after 9 and 12 cycles at the interval of 45 s (FIG. 8, Images A and B). Concentrated CY3 signals within the nuclear area were also evident. A similar pattern of CY3 signal was observed when the same AON was tagged with fluorescein (FIG. 8, Image C). However, cells exposed to CY3-tagged phosphorodiamidate morpholino oligomer (morpholino, charge neutral) with 420 W for 12 cycles did not show clearly detectable signals within the cells in any of the wells (data not shown). This result suggests that the delivery of transgenes by microwave irradiation is achieved not only through pore formation.

Figure 9:
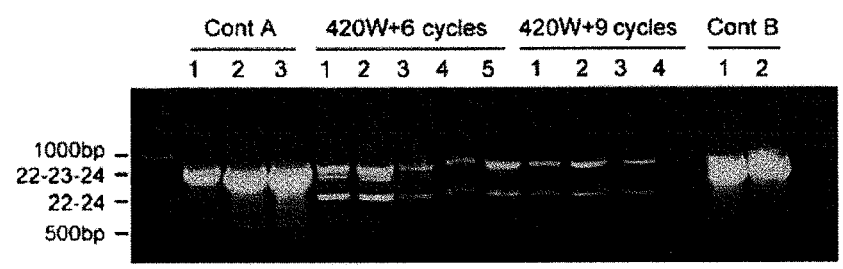
FIG. 9 illustrates dystrophin exon 23 skipping with the 2-O-methyl-phosphorothioate AON E23+2-18 in the C2C12 and H2K mdx myoblasts.

To examine whether the delivery of AON could lead to specific exon 23 skipping, the same power settings were used for the delivery of the untagged 2OMePS AON. Total RNA was extracted 24 h after microwave irradiation and reverse transcription (RT)-PCR was performed to amplify the sequence from exon 20-26 of the dystrophin mRNA. Cells with 240 W exposure showed a single band corresponding to the full-length dystrophin mRNA seen in the control samples, indicating no significant exon 23 skipping. However, the cells exposed to 420 W with both six and nine cycles showed clearly two bands, one with the size of the normal dystrophin mRNA and the other with the size approximately 200 bp smaller and corresponding to the dystrophin mRNA with exon 23 skipped (FIG. 9). FIG. 9 is related to dystrophin exon 23 skipping with 2'Omethyl phosphorothioate AON E23+2-18 in the C2C12 and H2K mdx myoblasts. As shown in FIG. 9, the samples in Cont (Control) A and B are from the cells incubated with AON E23+2-18, but without being exposed to microwave irradiation. RT-PCR products representing mRNA with exon 23 skipped (bands indicated by 22-24) were demonstrated with intensity approximately equal to that of the normal mRNA (bands indicated by 22-23-24) of the same samples. RNA was extracted from C2C12 cells and exposed to microwave radiation (i.e., irradiated with microwave energy) at a setting of 420 W for 6 or 9 cycles. Numbers 1-5 represent the repeats of the experiments. The signal intensity of the smaller RT-PCR products was at similar levels to that of the normal transcript. However, signals for both bands were considerably weaker in the cells after nine cycles of exposure when compared with the cells with six cycles of exposure. This is consistent with the fact that cells exposed to six cycles of microwave irradiation contained 85-90% control levels of mRNA, whereas extended cycles reduced the total amount of mRNA to 40-70% control levels 24 h after the microwave irradiation treatment.

Figure 10:
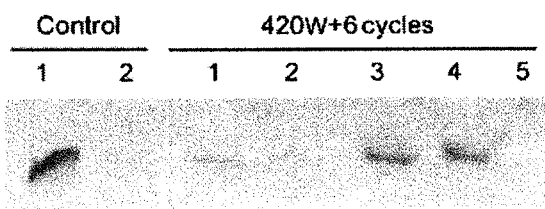
FIG. 10 shows a Western Blot analysis illustrating the relative detection of dystrophin.

To further investigate whether the effective exon skipping can restore dystrophin protein expression, H2K mdx myoblasts containing a nonsense point mutation in the exon 23 of the dystrophin gene were examined. The cells were incubated with the 2OMePS AON targeting exon 23 and exposed to microwave irradiation at a setting of 420 W with six and nine cycles. As the expression of dystrophin relies on differentiation of the myoblasts to myotubes, the microwave irradiation-treated H2K mdx myoblasts were cultured under differentiation condition for further 4 days. As shown in FIG. 10, dystrophin expression was then examined by western blots. The Western blot shown in FIG. 10 shows the detection of dystrophin protein in H2K mdx cells 4 days after microwave irradiation at 420 W for 6 cycles. Control 1 represents proteins from differentiated C2C12 cells while control 2 represents proteins from H2K mdx cells incubated with AON E23+2-18 without exposure to microwave irradiation. Lines 1-5 represent cells from different wells of the same 6 well plate. As shown in FIG. 10, the control H2K mdx cells without microwave irradiation treatment showed no dystrophin as the nonsense point mutation prevented the translation of dystrophin protein. In contrast, the cells treated with microwave irradiation clearly demonstrated detectable levels of dystrophin with the size of the protein similar to that of normal dystrophin expressed in the differentiated normal C2C12 cells. As expected, the levels of dystrophin in the cells of different wells of the same culture plate (under the same exposure of microwave irradiation) varied from approximately 50% of C2C12 cells to undetectable.

II. Summary of Results

As discussed above, microwave irradiation has been shown to effectively deliver antisense oligonulceotides into myoblasts, resulting in induction of specific skipping of mouse dystrophin exon 23 and restoration of dystrophin protein. Microwave irradiation also improves transgene expression, but only in restricted areas within the exposed culture cells. However, the failure to induce transgene expression homogeneously appears to be the result of high variability in the distribution of the magnetic field and the energy produced by the microwave irradiating device used in the study. The results of the study indicate that the use of microwave irradiation has the ability to provide a method for convenient delivery of nucleic acids and other macromolecules. However, the efficiency of delivery will increase upon new designs of microwave irradiating devices capable of providing a more controllable and evenly distributed energy level for homogenous exposure of the target cells as, but not limited to, illustrated herein.

As mentioned earlier, the mechanisms by which microwave irradiation improves the delivery of plasmid and oligo-nucleotides are not fully understood. The energy from microwave irradiation consists of an electric field and a magnetic field, but only the electric field is considered to transfer energy to a substance within its reach. This energy transfer is conducted through two mechanisms, dipole rotation and ionic conduction. Dipole rotation is the reaction of the polar molecules to align themselves to the electric field of the MW. This interaction is related to the polarity of the molecules and their ability to align with the electric field. Similarly, ionic conduction is the result of alignment of free ions or ionic species to the MW electric field. Although not desiring to be held to the following explanation, it is possible that the polar charges on the cell membrane molecules, such as proteins and lipids, may oscillate with the changing electric field of microwave irradiation, causing increased fluctuation of the cell membrane. These effects are similar to those proposed to explain the mechanisms of two other physical methods for gene transfer, electroporation and ultrasound irradiation. Microwave irradiation can also induce dipole rotation and ionic conduction on the nucleic acids, which may lead to rapid movement of the molecules with increased opportunity to interact with and pass through the cell membrane, resulting in an increase in cellular uptake of nucleic acids. The results, indicate that the efficiency of microwave irradiation on nucleic acid delivery may depend on the size of the molecules, with short oligonucleotides being delivered much more efficiently than large plasmid DNA.

A rapid rise in the temperature by microwave irradiation could also be responsible for increase in membrane permeability by enhancing the fluidity of the membrane molecules. However, Galvin et al. reported that an increase in membrane permeability does not depend on significant increase in system temperature. See Galvin M J, Hall C A, McRee D I. Microwave radiation effects on cardiac muscle cells in vitro. Radiat Res 1981; 86: 358-367. Similarly, attempts to measure the temperature at precise points of the culture wells during the microwave irradiation with the IR thermo imager (Raytek ThermoView Ti30) failed to reveal a definitive correlation between the temperature and the efficiency of transgene expression. In fact, the results suggest that increased temperature itself may not have direct effect on transgene expression and therefore a specific amount of local heating is neither a necessary component nor indicative of effective gene delivery.

Another notable observance is that the efficacy for the delivery of oligonucleotide can depend on the nature of the molecules. Although the negatively charged 2OMePS AON and the natural DNA oligonucleotide can be effectively delivered into the C2C12 cells, the exact same sequence of morpholino oligomers cannot be delivered with the same power settings. Morpholinos are polar, but non-charged molecules with phosphodiester bonds replaced by phosphoroamidate linkages and the ribose replaced by a morpholino moiety. See Summerton J, Weller D. Morpholino antisense oligomers: design, preparation, and properties. Antisense Nucleic Acid Drug Dev 1997; 7: 187-195. Although not wishing to be held to the following explanation, it is possible that the lack of charge in the morpholino molecules reduces the efficacy of microwave irradiation for their delivery into target cells or tissues. This would be consistent with a reduced dipole rotation and ionic conduction effect of microwave irradiation on the molecules. Furthermore, the electromagnetic field of microwave irradiation with the short pulse given in the study described above might produce electric current, difficult to be detected by existing means, but sufficient to force the small charged molecules such as the 2OMePS AON, not the neutral morpholino, to move into the already permeabilized cells.

This effect would be similar to that of electroporation with electric current forcing nucleic acid to pass through cell membrane.

As referenced above, one interesting observation relates to the variability of transgene delivery by microwave irradiation to the non-uniformity within the particular device used to emit the microwave radiation. For instance, transgene expression can be detected only in cells limited to small areas in some wells of a single six-well plate exposed to microwave radiation. However, this is expected considering the microwave energy level emitted by current commercially available devices is highly irregular in energy distribution. This irregularity occurs due to the absorption and refraction of microwave irradiation within the chamber, creating an uneven energy field. The variation in the shape and the material of cell culture plates can also affect the energy distribution as the microwave energy will interact differentially within. In the area where insufficient microwave energy is delivered, transfection is likely not to be achieved, whereas in the area with excessive microwave energy cells can be damaged. As such, cells should be exposed to an appropriate amount of microwave radiation during the irradiation step to achieve transfection and transgene expression, without significantly killing or damaging the targeted cells.

As demonstrated by the examples provided herein, appropriate irradiation settings are obtained for achieving delivery of macromolecules (e.g., genes and oligonucleotides) into target cells. This together with the ability of microwave irradiation to penetrate deep into tissues should enable such delivery methods to be used for gene and oligonucleotide delivery in vivo, particularly for targeting tissues and organs. As discussed herein, in vitro delivery of macromolecules can be achieved by exploiting the use of different frequencies and microwave emitting devices designed to provide controllable and more evenly distributed microwave energy at subcellular levels.

III. Samples of Materials, Preparation and Measurements

A. Cell Culture

C2C12 myoblast cells were grown in Dulbecco's modified Eagle's medium (DMEM) supplemented with 20% fetal bovine serum (Gibco, Carlsbad, Calif., USA), 2 mM L-glutamine (Gibco) and 100 U ml$^{-1}$ of penicillin/streptomycin (Gibco). Cells were incubated at 37° C. with 10% $CO_2$. Cell cultures were allowed to reach 70-80% confluence and then plated into six-well culture plates (Costar, Cambridge, Mass., USA) at 2×10$^5$ cells per well 24 h prior to microwave irradiation.

H2K mdx tsA58 myoblasts were grown at 33° C. in DMEM containing 20 U ml$^{-1}$ gamma interferon and 20% fetal bovine serum. The cells were subjected to microwave irradiation when they reached near confluence. After the treatment, the cells were grown in differentiation medium containing 5% horse serum at 37° C. for 4 days. C2C12 cells were also grown to confluence and then changed to the differentiation medium containing 5% horse serum at 37° C. for 4 days.

Immediately before microwave irradiation (e.g., exposure to microwave radiation), cells were washed with phosphate-buffered saline and fresh DMEM medium was added together with 4 μg of reporter gene or oligonucleotide to each well. The plate was immediately placed in the middle of the turntable in the microwave irradiating device for exposure.

B. Reporter Genes and Expression Detection pEGFP-N3 vector expressing a green fluorescent protein and pRL-CMV, a *Renilla* luciferase expression vector was utilized. The plasmids were propagated, harvested, purified using a Qiagen endotoxin-free purification kit and stored in endotoxin-free $H_2O$ at 1 μg μl$^-$. Renilla luciferase expression was measured using a Renilla Luciferase Assay kit (Promega, Madison, Wis., USA). Cells were washed with phosphate-buffered saline, lysed and the lysate was collected according to the manufacturer's instructions. Luminescent signal was quantified using a Turner Biosystems 20/20 single tube luminometer. A portion of 20 μl of lysate was combined with 100 μl of *Renilla* luciferase assay reagent and placed into the luminometer. *Renilla* luciferase activity was recorded as relative light units (RLU). Expression of pEGFP-N3 vector was viewed and images were captured directly under a fluorescein isothiocyanate filter using an IX71 inverted research microscope (Olympus, Center Valley, Pa., USA).

C. Power Level and Cycle Settings of MW Irradiation

Power levels and cycles were set up and saved as programs in the MARS 5 system (CEM, Charlotte, N.C., USA). The base setting of 1200 W was used to produce 240, 420 and 600 W output setting by limiting the percentage of time the cavity was exposed to the magnetron for 20, 35 and 50%, respectively. Each exposure lasted 5 s and varying number of repeats (cycles) was given with a 45-s interval of time. Controls for each group were placed in the same medium for same time period with same amount of plasmid DNA or nucleotides, but without exposure to microwave irradiation. Following exposure, the medium was removed and cells were washed with DMEM. Normal growth medium (2 ml) was added for each well and cells were incubated at 37° C. with 10% $CO_2$ for 24 h.

D. AON, RNA Extraction and RT-PCR

AON M23D (+02-1 8) (5'-GGCCAAACCTCGGCT-TACCT-3') (SEQ ID NO:1) against the boundary sequences of exon and intron 23 of mouse dystrophin gene and the sense oligonucleotide (5'-AGGTAAGCCGAGGTTTGGCC-3')U (SEQ ID NO:2) as 2'O methyl-phosphorothioate (IDT, Coralville, Iowa, USA) and phosphorodiamidates morpholino (morpholinos; GeneTools, Philomath, Oreg., USA). CY3- and fluorescein-tagged 2'O methyl-phosphorothioate (IDT) and CY3-tagged morpholino (GeneTools) were also used. C2C12 cells in each well of the six-well plate were exposed to 4 μg of oligonucleotides. Following exposure, the cells were washed with DMEM, added with 2 ml of C2C12 growth medium and incubated for 24 h. The cells were trypsinized, centrifuged and pelleted. Total RNA was then extracted and 200 ng of RNA template was used for a 25 μl RT-PCR reaction with the Qiagen one-step RT-PCR kit (Qiagen, Valencia, Calif., USA). The primer sequences for the RT-PCR reaction were Ex20Fo 5'-CAGAATTCTGCCAATTGCTGAG-3' (SEQ ID NO:3) and Ex26Ro 5'-TTCTTCAGCTTGTGT-CATCC-3' (SEQ ID NO:4) for amplification of mRNA from exon 20 to 26." The cycling conditions were 95° C. for 1 min, 55° C. for 1 min, 72° C. for 2 min for 30 cycles. The reaction mix consists of 1×PCR buffer (Invitrogen), 10 μM of each dNTP, 0.6 μM of each primer and 2.5 mM $MgCl_2$. Products were examined by electrophoresis on a 2% agarose gel. RNA extracted from muscle of C57B1/10ScSn (C57B1/10) and C2C12 cells was used as control. RT-PCR amplifies normal dystrophin mRNA as a 901-bp band and dystrophin mRNA with exon 23 skipping as a 688-bp band. The bands with expected size for the transcript with exon 23 deleted were also extracted and sequenced.

E. Cell Viability

To assess cell viability following microwave irradiation, a CellTiter-Glo Luminescent Cell Viability Assay kit (Promega) was used. Luminescent signal is proportional to the amount of ATP present. Cell plate was allowed to cool to room temperature for 24 h following exposure to microwave radiation. CellTiter-Glo reagent (100 μl) was added directly into each well of six-well plate. Plate was allowed to rock on an orbital shaker for 2 min and to stabilize for 10 min following mixing. Turner Biosystems 20/20 single tube luminometer was adjusted to 4 s integration time without any delay. Here, 100 μl of each cell medium/CellTiter-Glo reagent was added to 12 mm×50 mm disposable cuvette (Promega) and placed in luminometer for measurement.

F. Temperature Measurement

An IR thermo imager (Raytek ThermoView Ti30) was used to capture the thermo signature. On completion of the designated exposure cycle(s), the plate was quickly moved from the cavity of the MARS and set down on a flat insulated surface. The IR imager was directed at the plate from above at an approximate distance of 12 inches and the IR imager was captured. The time that elapsed to move the plate to a suitable surface and capture the image was between 5 and 7 s. These images were uploaded to the computer and analyzed using InsideIR Software. The images produced are color-coded IR heat signatures that correspond to the heat scale generated by the software. Images were taken at 400 W 5 s×12 with 45-s intervals and compared with the luciferase and eGFP expression at the same setting recorded earlier.

G. Immunocytochemistry

All cells in the wells were collected 48 h after microwave irradiation and washed. The cells were attached onto glass slides, dried and stored at −20° C. The cells were permeabilized with acetone at −20° C. for 10 minutes and washed twice with phosphate-buffered saline. The cells were then incubated with primary antibody to cleaved caspase 3 (Asp 175, Alexa 488 conjugated; 1:100; Beckman Coulter, Fullerton, Calif., USA). Cells treated with 1 mmol $H_2O_2$ in DMEM were used as a positive control.

H. Protein Extraction and Western Blot

Microwave irradiation-treated H2K mdx myoblasts were grown in differentiation medium for 4 days, and the cells were collected and lysed with 200 μl protein extraction buffer as described earlier. The protein concentration was quantified by Protein Assay kit (Bio-Rad, Hercules, Calif., USA). Differentiated C2C12 cells were used as positive controls. Equal amount of proteins from each sample was loaded onto a 6% polyacrylamide gel containing 0.2% SDS and 10% glycerol. Samples were electrophoresed overnight at 10 mA at 4° C. and blotted onto nitrocellulose membrane overnight at 300 mA. The membrane was then washed and blocked with 5% skimmed milk and probed with monoclonal antibody NCL-DYS1 against dystrophin rod domain (Vector Labs, Burlingame, Calif., USA) overnight. The bound primary antibody was detected by horseradish peroxidase-conjugated goat anti-mouse IgG and ECL Western Blotting Analysis System (Perkin Elmer, Waltham, Mass., USA).

Many modifications and other embodiments of the invention set forth herein will come to mind to one skilled in the art to which these inventions pertain having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of delivering macromolecules into a target cell or tissue, comprising:
   (i) exposing a target cell or tissue to at least one macromolecule;
   (ii) irradiating the target cell or tissue with microwave radiation to increase the transmembrane diffusive permeability of the target cell or tissue such that the at least one macromolecule can be inserted into the target cell or tissue; and
   (iii) inserting the at least one macromolecule into the target cell or tissue.

2. The method of claim 1, wherein the step of irradiating increases the transmembrane diffusive permeability of the target cell or tissue by one of the following: (a) forming one or more pores in at least a portion of the target cell or tissue; (b) enhancing binding of the at least one macromolecule to the target cell or tissue's membrane; or (c) a combination of forming pores and enhancing the binding of the at least one macromolecule to the membrane of the target cell or tissue.

3. The method of claim 1, wherein the microwave radiation has a power from about 50 Watts to 5000 Watts.

4. The method of claim 1, wherein the microwave radiation is cyclically applied in a series of one or more cycles; wherein each cycle comprises a time duration in which the targeted cell or tissue is exposed to the microwave radiation and a second time duration in which the targeted cell or tissue is not exposed to the microwave radiation.

5. The method of claim 4, wherein the time duration in which the targeted cell or tissue is exposed to the microwave radiation is the same as the time duration in which the targeted cell or tissue is not exposed to the microwave radiation.

6. The method of claim 4, wherein the time duration in which the targeted cell or tissue is exposed to the microwave radiation is different than the time duration in which the targeted cell or tissue is not exposed to the microwave radiation.

7. The method of claim 4, wherein the microwave radiation is applied in a series of 1 to 100 cycles.

8. The method of claim 4, wherein the time duration in which the targeted cell or tissue is exposed to the microwave radiation ranges from 1 millisecond to 5 minutes.

9. The method of claim 1, wherein the at least one macromolecule comprises a biopolymer selected from the group consisting of DNA, plasmid DNA, RNA, proteins, carbohydrates, oligonucleotides, lipids, and combinations thereof.

10. The method of claim 9, wherein the oligonucleotides include oligomers with activity to bind a complementary DNA, RNA or protein sequences, wherein the oligomers can have different linkages between the monomers.

11. The method of claim 9, wherein the oligonucleotides/oligomers include a modified functional group, wherein the oligonucleotides/oligomers retain the ability to bind to complimentary DNA, RNA, or protein molecules.

12. The method of claim 9, wherein the oligonucleotides are suitable for interference of gene expression, protein function, splicing regulation or modification of genomic sequence.

13. The method of claim 1, wherein the at least one macromolecule is formulated with an additional reagent or reagents suitable for enhancing the delivery of the at least one macromolecule.

14. The method of claim 1, wherein cell or tissue comprises a local area on or within a living organism and the cell or tissue is irradiated in vivo.

15. The method of claim 14, wherein the local area comprises either an entire internal organ or a part of an internal organ.

16. The method of 1, wherein the targeted cell or tissue comprises the entire living organism, such that the at least one macromolecule is systemically delivered.

17. The method of claim 1, further comprising the co-delivery of the at least one macromolecule via a second delivery method selected from virus-mediated, non-viral biochemical vectors, electroporation, lipopolymers, cationic polymers, microbubbles and sonoporation; wherein the second delivery method further enhances the delivery efficiency of the at least one macromolecule.

18. A method of delivering macromolecules to a target cell, comprising:
   (i) providing a cell culture comprising a target cell in a suitable culture medium;
   (ii) adding at least one macromolecule into the cell culture; and
   (iii) exposing the cell culture to microwave radiation to increase the transmembrane diffusive permeability of the target cell such that the at least one macromolecule can be inserted into the target cell; and
   (iv) inserting at least one macromolecule into the target cell.

19. A method of delivering macromolecules to a target cell or tissue on or within a living organism, comprising:
   (i) administering at least one macromolecule into or near the target cell or tissue;
   (ii) exposing the target cell or tissue to microwave radiation to increase the transmembrane diffusive permeability of the target cell such that the at least one macromolecule can be inserted into the target cell or tissue; and
   (iii) inserting the at least one macromolecule into the target cell or tissue.

20. The method of claim 19, wherein the target cell or tissue comprises an internal organ of a living organism.

21. The method of claim 19, further comprising aligning the target cell or tissue with a microwave radiation source via a microwave irradiation path chamber operatively connected to the radiation source; wherein the path chamber conducts the microwave radiation to the targeted cell or tissue.

22. The method of claim 21, wherein the alignment of the target cell or tissue with the microwave radiation source comprises inserting the microwave irradiation path chamber through a canula which has been inserted into the living organism; wherein the microwave irradiation path chamber terminates proximate to and aligned with the target cell or tissue.

23. The method of claim 1, further comprising the steps of:
(i) removing the cell or tissue from a living organism and placing the cell in a viable medium prior to adding the macromolecule to the cell and exposing the cell to microwave radiation; and
(ii) infusing the treated cell back into the living organism.

* * * * *

UNITED STATES PATENT AND TRADEMARK OFFICE
CERTIFICATE OF CORRECTION

PATENT NO.       : 8,569,251 B2  
APPLICATION NO.  : 12/712580  
DATED            : October 29, 2013  
INVENTOR(S)      : Lu et al.

Page 1 of 1

It is certified that error appears in the above-identified patent and that said Letters Patent is hereby corrected as shown below:

Title page,
Item (73) Assignee: "The Charlotte-Mecklenburg Hospital Authority" should read --The Charlotte-Mecklenburg Hospital Authority d/b/a Carolinas Medical Center--.

Signed and Sealed this
Twenty-fifth Day of February, 2014

Michelle K. Lee
*Deputy Director of the United States Patent and Trademark Office*